United States Patent
Luhta et al.

(10) Patent No.: US 8,710,448 B2
(45) Date of Patent: Apr. 29, 2014

(54) RADIATION DETECTOR ARRAY

(75) Inventors: Randall P. Luhta, Highland Heights, OH (US); Marc A. Chappo, Elyria, OH (US); Brian E. Harwood, Wickliffe, OH (US); Rodney A. Mattson, Mentor, OH (US); Chris J. Vrettos, Willoughby, OH (US)

(73) Assignee: Koninklijke Philips N.V., Eindhoven (NL)

( * ) Notice: Subject to any disclaimer, the term of this patent is extended or adjusted under 35 U.S.C. 154(b) by 795 days.

(21) Appl. No.: 12/293,842

(22) PCT Filed: Mar. 8, 2007

(86) PCT No.: PCT/US2007/063532
§ 371 (c)(1),
(2), (4) Date: Sep. 22, 2008

(87) PCT Pub. No.: WO2007/117799
PCT Pub. Date: Oct. 18, 2007

(65) Prior Publication Data
US 2009/0121146 A1 May 14, 2009

Related U.S. Application Data

(60) Provisional application No. 60/743,976, filed on Mar. 30, 2006.

(51) Int. Cl.
*G01T 1/20* (2006.01)
*H01L 31/00* (2006.01)

(52) U.S. Cl.
USPC .............. 250/370.11; 250/370.09; 257/446; 257/459

(58) Field of Classification Search
USPC .......... 257/433, 431, 432, E21.705, 446, 457, 257/759, E31.092; 250/370.11, 370.09
See application file for complete search history.

(56) References Cited

U.S. PATENT DOCUMENTS

| | | | |
|---|---|---|---|
| 6,426,991 B1 * | 7/2002 | Mattson et al. | 378/19 |
| 6,510,195 B1 | 1/2003 | Chappo et al. | |
| 2003/0200655 A1 | 10/2003 | Vafi et al. | |
| 2003/0218120 A1 * | 11/2003 | Shibayama | 250/214.1 |

(Continued)

FOREIGN PATENT DOCUMENTS

| EP | 1492168 A1 | 12/2004 |
|---|---|---|
| EP | 1589582 A1 | 10/2005 |

OTHER PUBLICATIONS

Henry Ott, "Grounding of Mixed Signal PCBs," published Dec. 13, 2004, retreived from Internet [Oct. 29, 2012], retrieved from URL: <http//www.hottconsultants.com/techtips/split-gnd-plane.html>.*

(Continued)

*Primary Examiner* — David Porta
*Assistant Examiner* — Yara B Green

(57) ABSTRACT

A radiation detector module (22) particularly well suited for use in computed tomography (CT) applications includes a scintillator (200), a photodetector array (202), and signal processing electronics (205). The photodetector array (202) includes a semiconductor substrate (208) having a plurality of photodetectors and metalization (210) fabricated on non-illuminated side of the substrate (208). The metalization routes electrical signals between the photodetectors and the signal processing electronics (205) and between the signal processing electronics (205) and an electrical connector (209).

19 Claims, 14 Drawing Sheets

(56) References Cited

U.S. PATENT DOCUMENTS

| | | |
|---|---|---|
| 2003/0234363 A1 | 12/2003 | Sekine et al. |
| 2004/0032371 A1* | 2/2004 | Mendolia et al. ............. 343/702 |
| 2004/0256568 A1 | 12/2004 | Sekine et al. |
| 2005/0017345 A1* | 1/2005 | Sathe ........................... 257/700 |
| 2005/0040316 A1* | 2/2005 | Holm et al. ................ 250/208.1 |
| 2005/0139757 A1 | 6/2005 | Iwanczyk et al. |
| 2005/0141048 A1* | 6/2005 | Mizutani ...................... 358/474 |
| 2005/0167603 A1 | 8/2005 | Hoffman |
| 2006/0131707 A1* | 6/2006 | Carberry et al. ............. 257/676 |
| 2006/0157854 A1* | 7/2006 | Takewaki et al. ............ 257/758 |

OTHER PUBLICATIONS

Rochas, A., et al.; First Fully Integrated 2-D Array of Single-Photon Detectors in Standard CMOS Technology; 2003; IEEE Photonics Technology Letters; 15(7)963-965.

* cited by examiner

RADIATION DETECTOR ARRAY

CROSS REFERENCE TO RELATED APPLICATIONS

This application claims the benefit of U.S. provisional application Ser. No. 60/743,976 filed Mar. 30, 2006, which is incorporated herein by reference.

The present invention relates to x-ray detector arrays for use in computed tomography (CT) systems. It also finds application to the detection of radiation other than x-radiation and in other medical and non-medical applications where arrays of radiation sensitive detectors are required.

CT scanners have proven to be invaluable in providing information indicative of the internal structure of an object. In medical imaging, for example, CT scanners are widely used to provide images and other information indicative of the physiology of human patients. Recent years have seen the rapid adoption of multi-slice CT, as increasing the number of slices or channels can have a number of advantages, such as an improved ability to scan the heart and other moving portions of the anatomy, shorter scan times, improved scanner throughput, improved axial resolution and coverage, and the like.

One consequence of this trend, however, is that the requisite x-ray detectors are becoming increasingly complex and expensive. Indeed, the detector is often one of the most expensive components, if not the most expensive component, of a CT scanner. By way of one example, state of the art CT scanners are designed to acquire as many as 128 slices in one gantry revolution, and an exemplary detector system may require upwards of 80,000 individual detector elements or pixels.

The situation is further complicated by the fact that gaps or spaces between the pixels in the array can have a deleterious effect on image quality. This requirement tends to limit the space available for routing of the detector signals and for the required readout electronics, which are advantageously located in the space behind the detectors.

A two-dimensional (2D) detector system suitable for use in multi-slice CT scanners is disclosed in U.S. Pat. No. 6,510,195, entitled Solid State X-Radiation Detector Modules and Mosaics Thereof, and an Imaging Method and Apparatus for Employing Same, which patent is expressly incorporated by reference in its entirety herein. As discussed more fully in the patent, the detector modules in such a system have included a scintillator in optical communication with a photodiode array. A metalization layer having a plurality metal pads located on the non-illuminated side of photodiode array has provided electrical contact to the various photodiodes. The pads have conformed to the pitch and spacing of the photodiodes. Consequently, the pads have in turn been bump bonded to a separate carrier substrate. The carrier substrate has in turn included a plurality of conductive layers arranged into a circuit pattern and connected to contact pads on the other side of the substrate. The contact pads provide connection points for the readout electronics. In another disclosed embodiment, an ASIC having input connections which match the pitch and spacing of the photodiodes has been connected directly to the pads. A number of detector modules have been assembled so as to form a 2D tiled array.

While such a detector system is indeed effective, there remains room for improvement. For example, it remains desirable to further reduce the cost of the detector, simplify the manufacturing process, and to improve the flexibility and reliability of the detector design.

Aspects of the present invention address these matters, and others.

According to a first aspect of the invention, a radiation detector includes a scintillator, a photodetector array, and signal processing electronics. The photodetector array includes a semiconductor substrate including a plurality of photodetector elements in optical communication with the scintillator, and metalization formed on a side of the semiconductor substrate opposite the scintillator. The signal processing electronics are carried on a side of the photodetector array opposite the scintillator. The metalization includes a first plurality of contacts electrically connected to the photodetector elements and a second plurality of contacts in electrical communication with the first plurality of contacts and the signal processing electronics.

According to another aspect of the invention, a radiation detector includes a semiconductor substrate having a radiation receiving face and a two dimensional array of radiation sensitive detector elements which detect radiation received by the radiation receiving face. The detector includes metalization formed on a side of the semiconductor substrate opposite the radiation receiving face, the metalization includes first contacts and second contacts. The first contacts are electrically connected to the array of photodetector elements and the metalization is configured to route electrical signals from the first contacts to the second contacts.

According to another aspect, an apparatus includes an examination region, an object support which supports an object in the examination region, a plurality of radiation detector modules disposed in a two-dimensional array. The detector modules comprise include a photodetector array which includes a semiconductor substrate having a radiation receiving face which faces the examination region and an array of radiation sensitive detectors. The detector modules also includes at least a first electrical signal routing layer formed on a side of the semiconductor substrate opposite the radiation receiving face using a semiconductor fabrication technique, and signal processing electronics (205) carried by the photodetector array. The at least a first signal routing layer is disposed physically between the semiconductor substrate and the signal processing electronics, and the at least a first electrical signal routing layer is electrically connected to signal processing electronics.

Those skilled in the art will appreciate still other aspects of the present invention upon reading and understanding the attached figures and description.

The present invention is illustrated by way of example and not limitation in the figures of the accompanying drawings, in which like references indicate similar elements and in which:

FIG. 1 depicts a CT scanner.

FIGS. 2A, 2B, and 2C depict a detector module.

FIGS. 3A, 3B, 3C, and 3D depict a photodetector array and certain related components.

FIGS. 6A, 6B, 6C, 6D, and 6E depict a detector module during various stages of its manufacture.

Figure 7A:
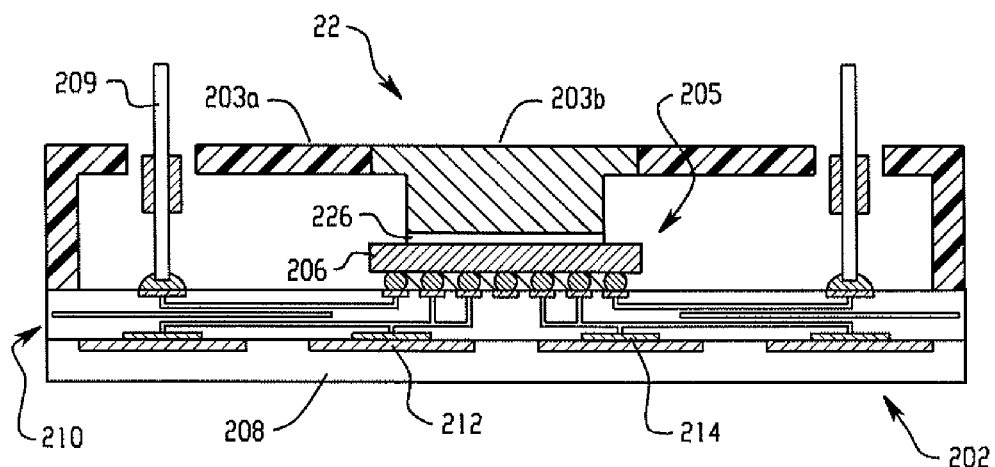
Figure 7B:
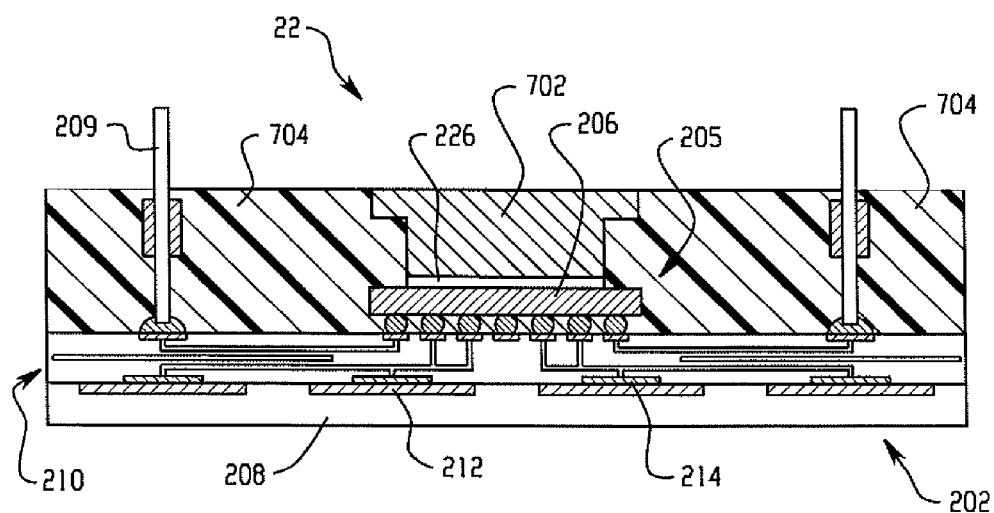

FIGS. 7A and 7B depict cover arrangement for a detector module.

Figure 8A:
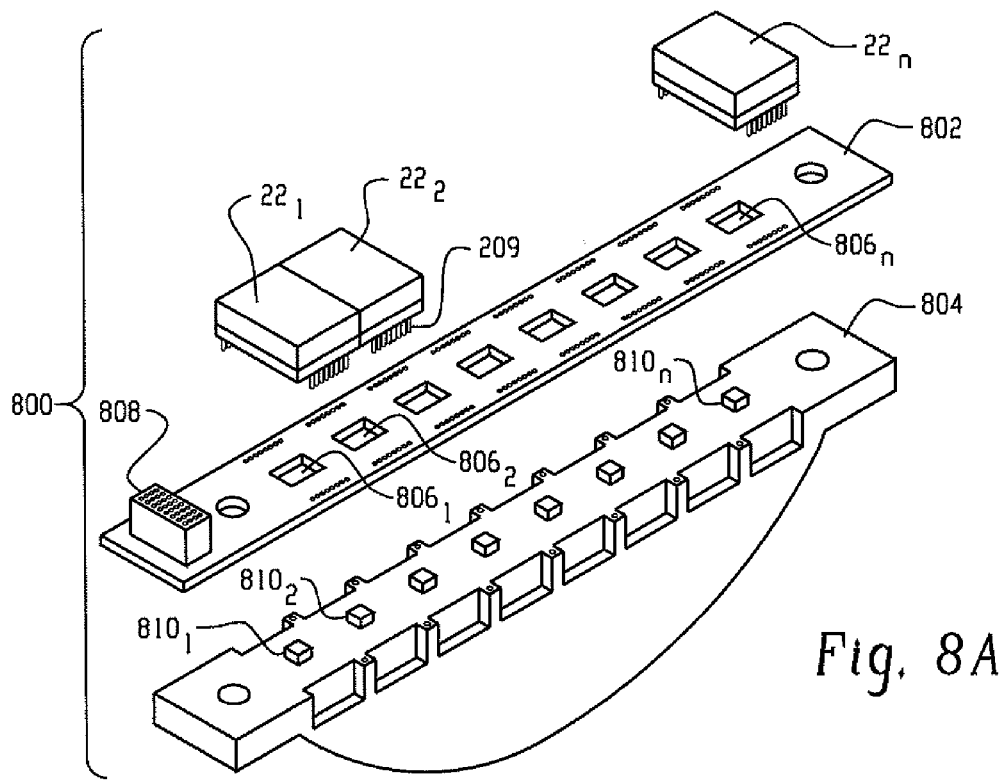
Figure 8B:
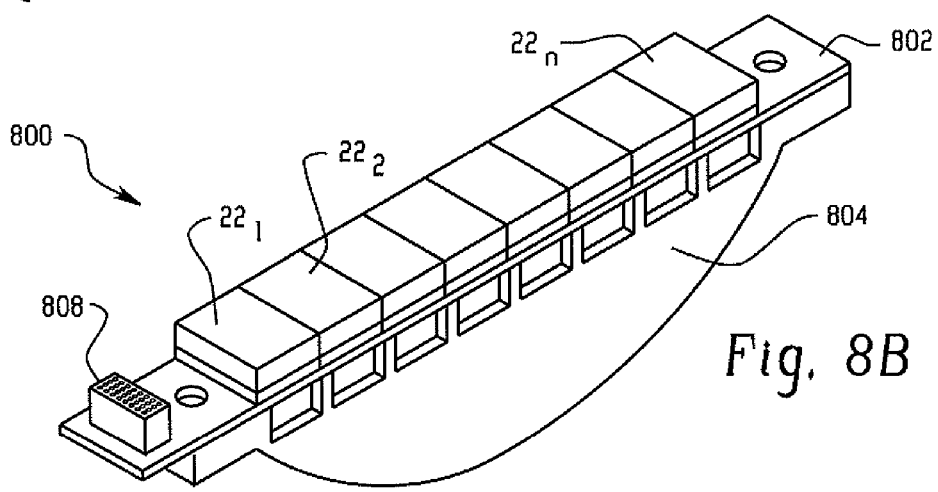
Figure 8C:
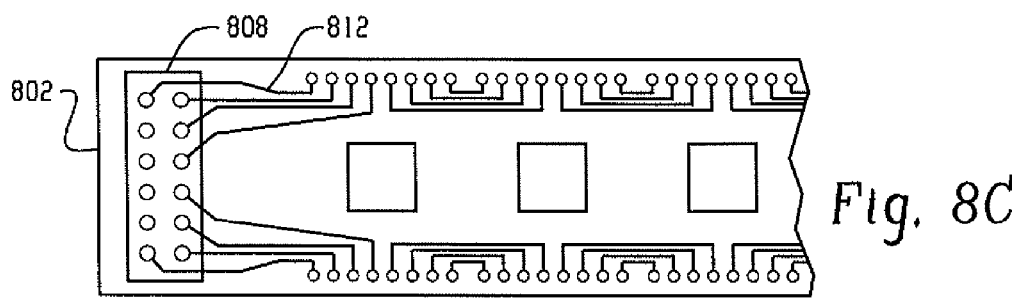

FIGS. 8A, 8B, and 8C depict a detector subassembly.

Figure 9A:
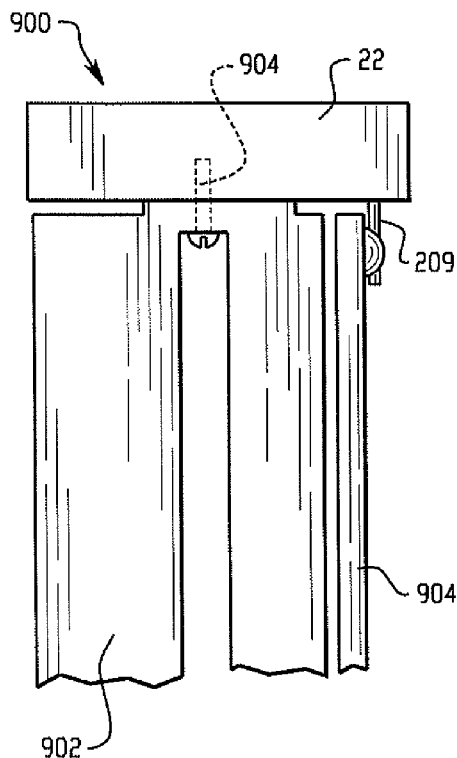
Figure 9B:
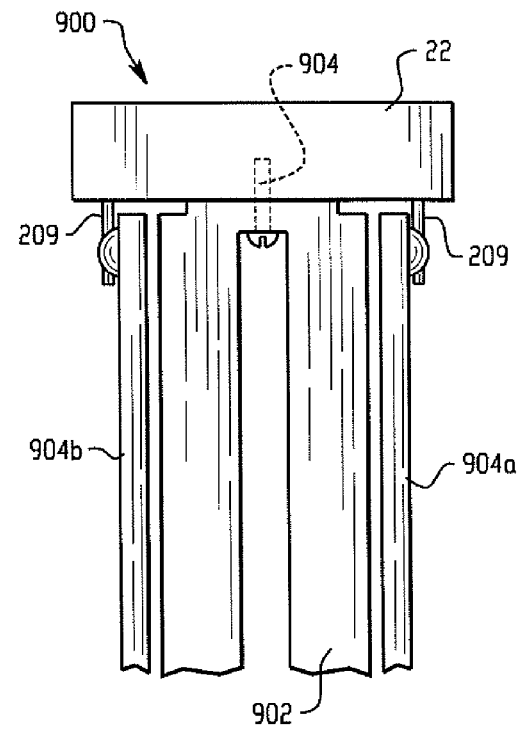
Figure 9C:
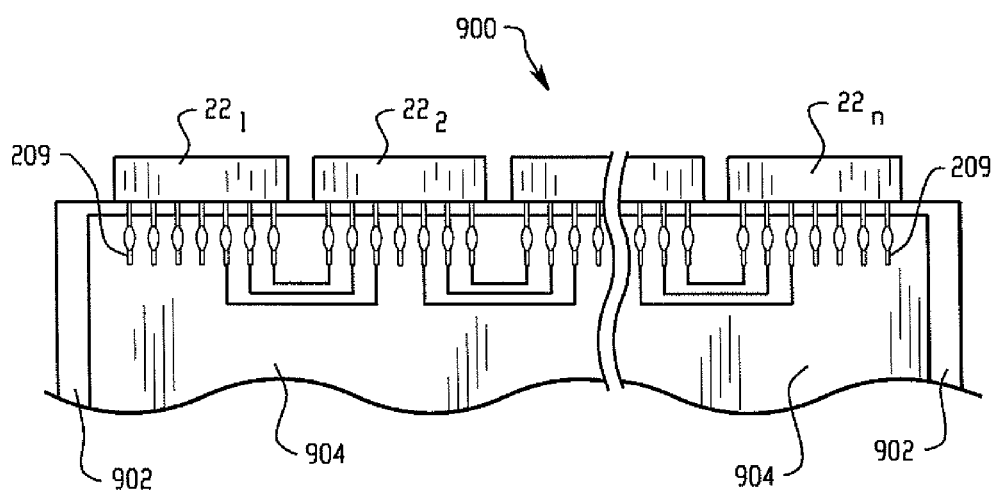

FIGS. 9A, 9B, and 9C depict a detector subassembly.

Figures 10A, 10B:
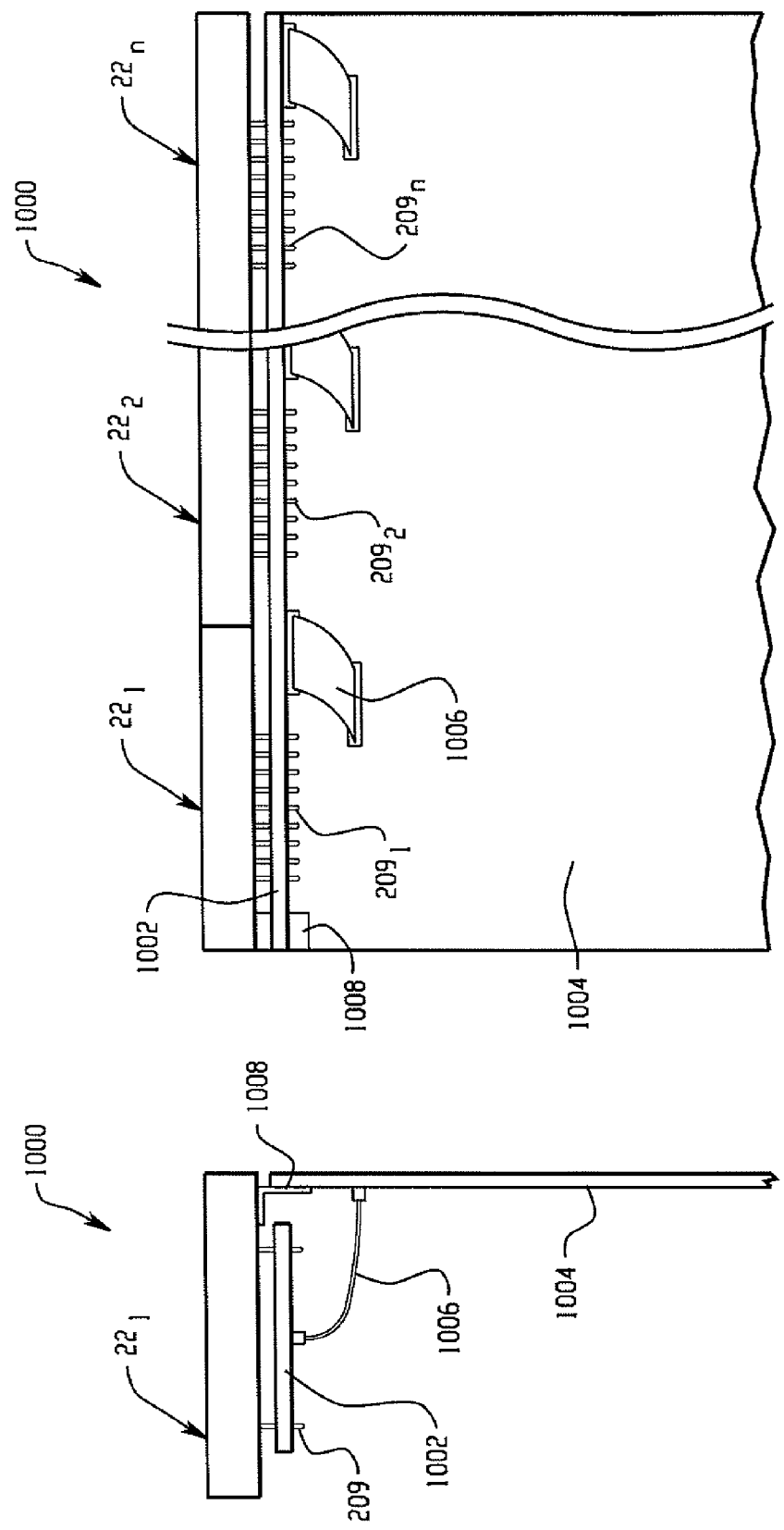

FIGS. 10A and 10B depict a detector subassembly.

Figure 11:
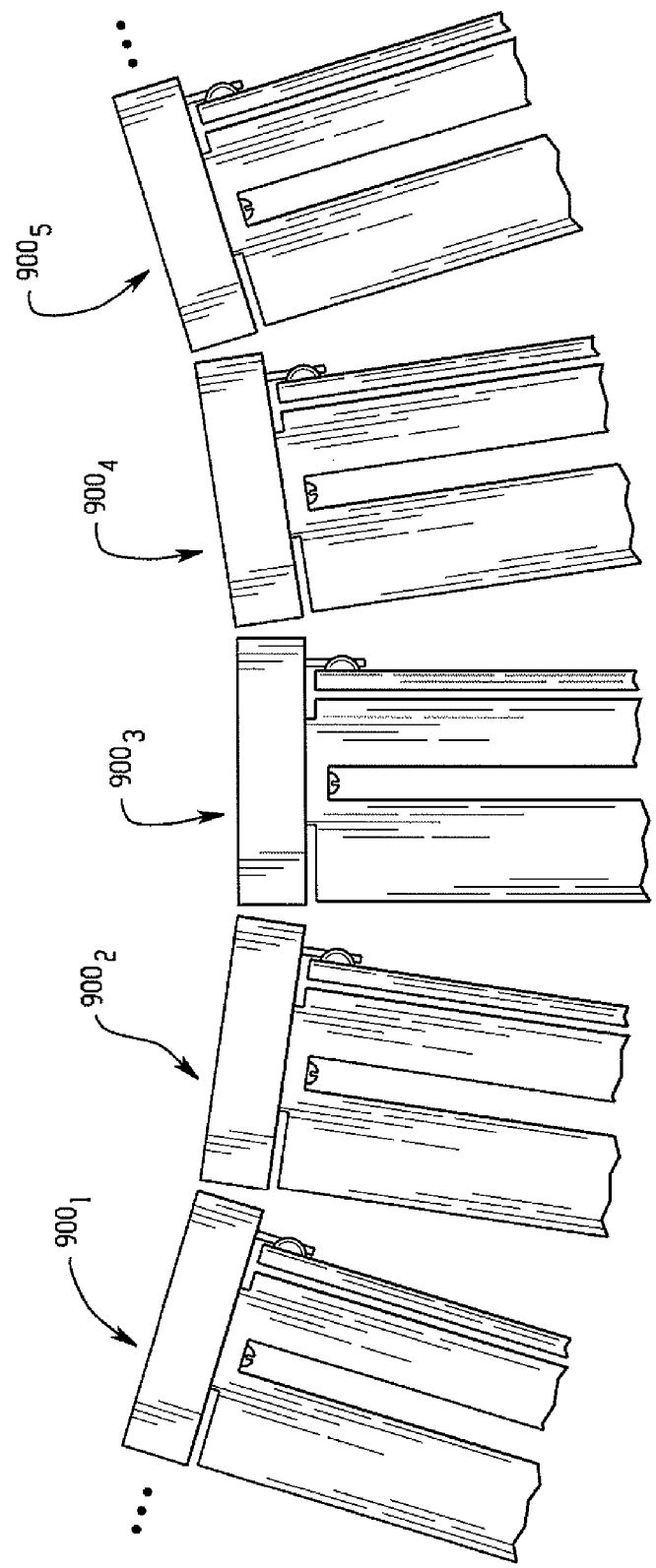

FIG. 11 depicts detector subassemblies arranged to form a portion of an arcuate detector.

Figure 1:
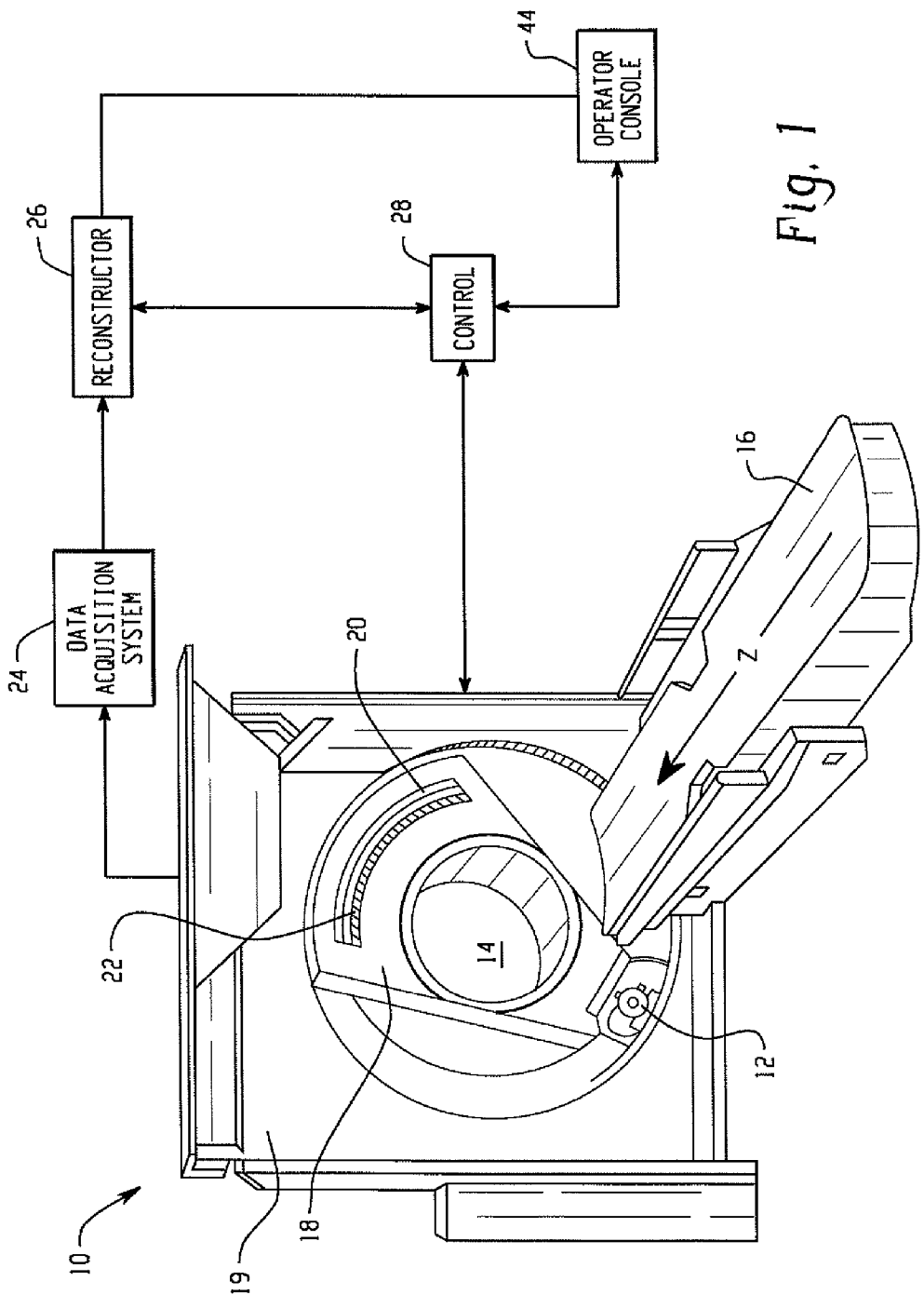

With reference to FIG. 1, a CT scanner 10 includes a rotating gantry portion 18 which rotates about an examination region 14 and a stationary gantry portion 19. The rotating gantry 18 supports a radiation source 12 such as an x-ray tube. The rotating gantry 18 also supports an x-ray sensitive detector 20 which subtends an arc on the opposite side of the examination region 14. X-rays produced by the x-ray source 12 traverse the examination region 14 and are detected by the detector 20. An object support 16 supports an object such as human patient in the examination region 14. The support 16 is preferably movable in coordination with the rotation of the gantry 18 so as to provide helical scanning.

The detector 20 includes a plurality of detector modules 22, with each module 22 including an array of radiation sensitive detector pixels. A plurality of detector modules 22 are arranged so as to form a generally arcuate, two-dimensional (2D) tiled detector array in which pixels in of the various detector modules 22 abut or are otherwise substantially adjacent to pixels in one or more adjacent modules 22. As will be further discussed below, the detector modules 22 are advantageously fabricated using back illuminated photodiode (BIP) arrays having one more metalization layers and corresponding electrical contacts fabricated on their non-illuminated side. Readout electronics carried by the detector array and connected to the contact provide multiplexers, amplifiers, analog to digital converters, and the like which convert the relatively low level analog signals produced by the photodetectors to digital signals.

In one implementation, the detector 20 includes one hundred twenty eight (128) or more slices. Note also that the detector modules 22 or the detector pixels included therein may be arranged so that the detector array is irregular. For example, pixels in one or more rows or columns may be offset from one another. A so-called fourth generation scanner configuration, in which the detector 20 spans an arc of 360 degrees and remains stationary while the x-ray source 12 rotates, as well as flat panel detectors, may also be implemented. Detector having greater or lesser number of slices may likewise be implemented.

A data acquisition system 24 preferably carried by the rotating gantry 18 receives output signals from a plurality of detector modules 22 and provides additional multiplexing, data communication, and like functionality. A reconstructor 26 reconstructs the data obtained by the detector 20 to form volumetric image data indicative of the object under examination.

A general purpose computer serves as an operator console 44. The console 44 includes a human-readable output device such as a monitor or display and an input device such as a keyboard and mouse. Software resident on the console allows the operator to control the operation of the scanner by establishing desired scan protocols, initiating and terminating scans, viewing and otherwise manipulating the volumetric image data, and otherwise interacting with the scanner.

A controller 28 coordinates the various scan parameters as necessary to carry out a desired scan protocol, including x-ray source 12 parameters, movement of the patient couch 16, and operation of the data acquisition system 26.

Figure 2A:
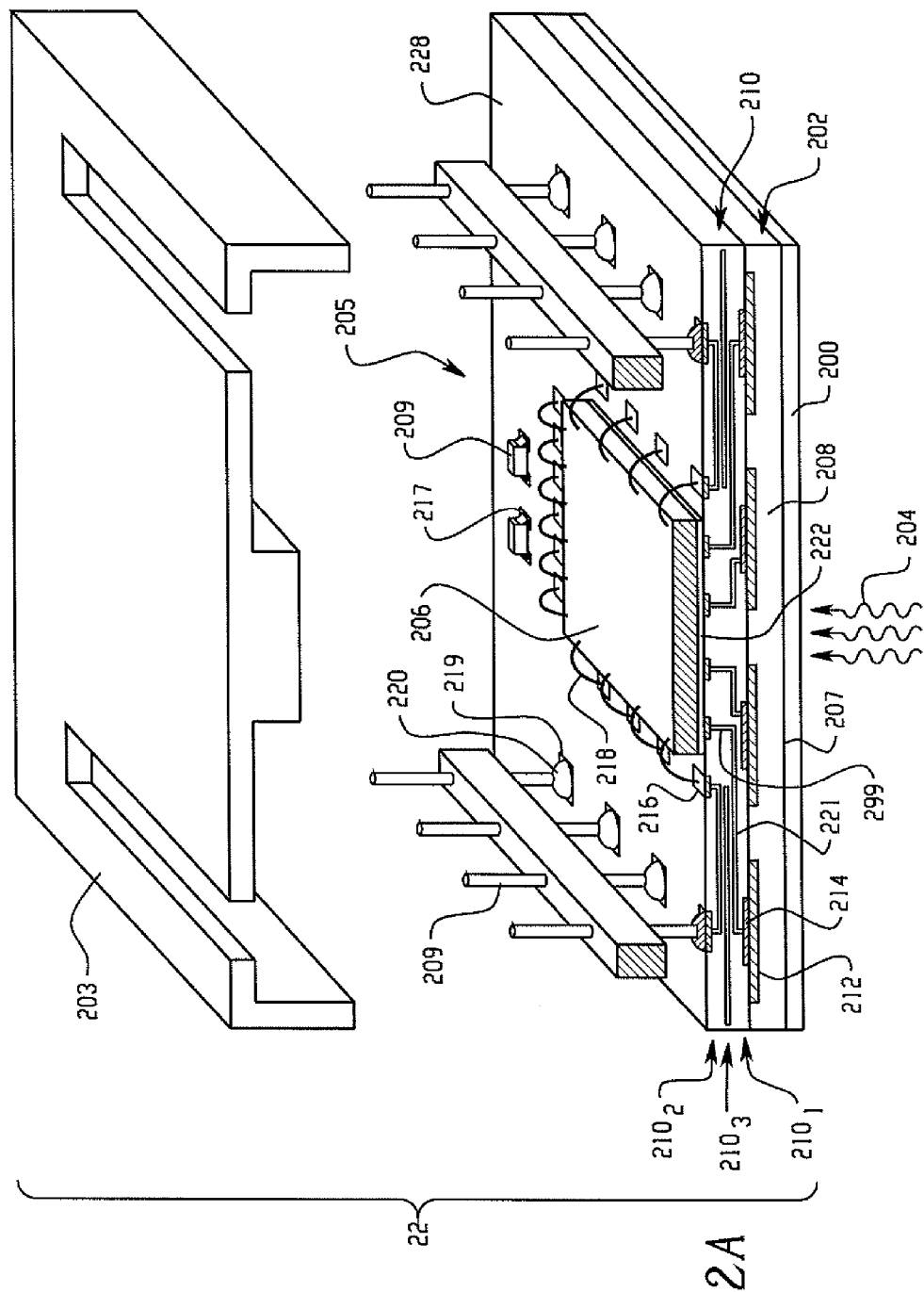
Figure 2B:
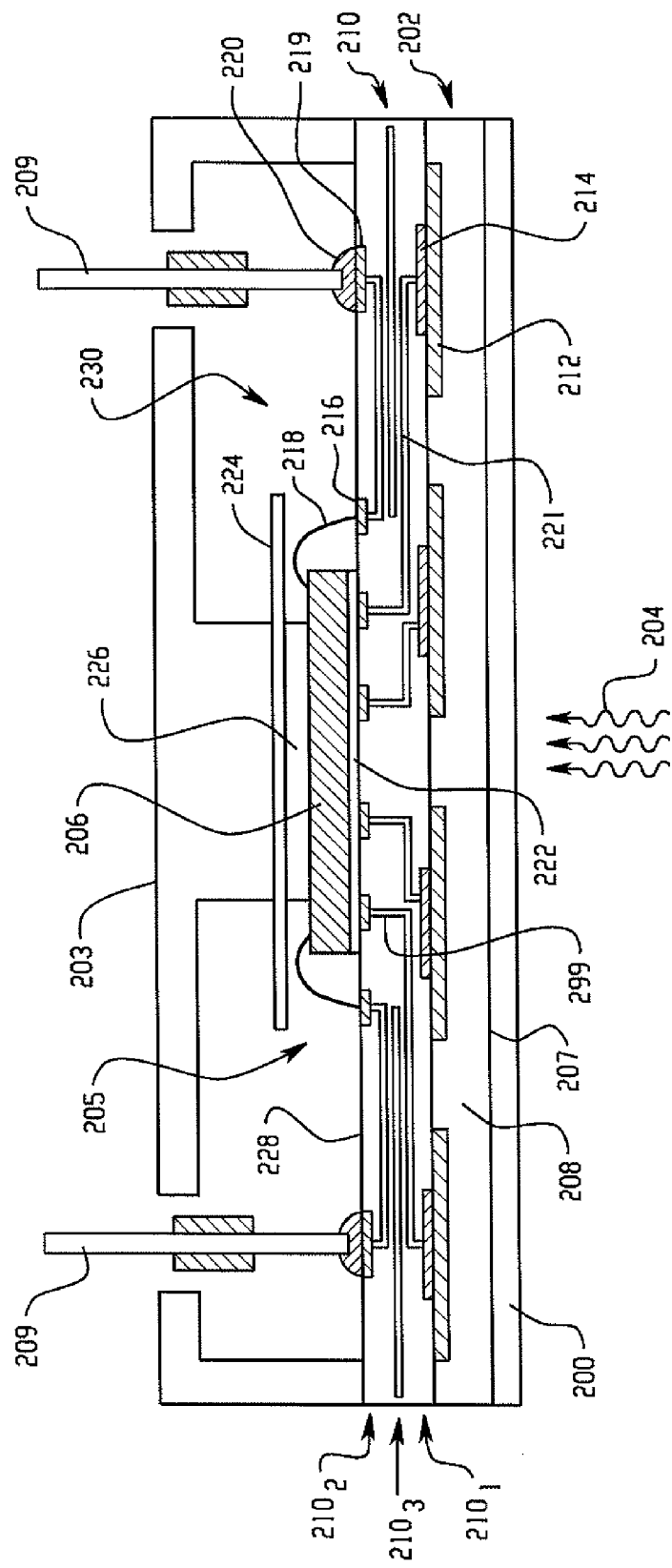
Figure 2C:
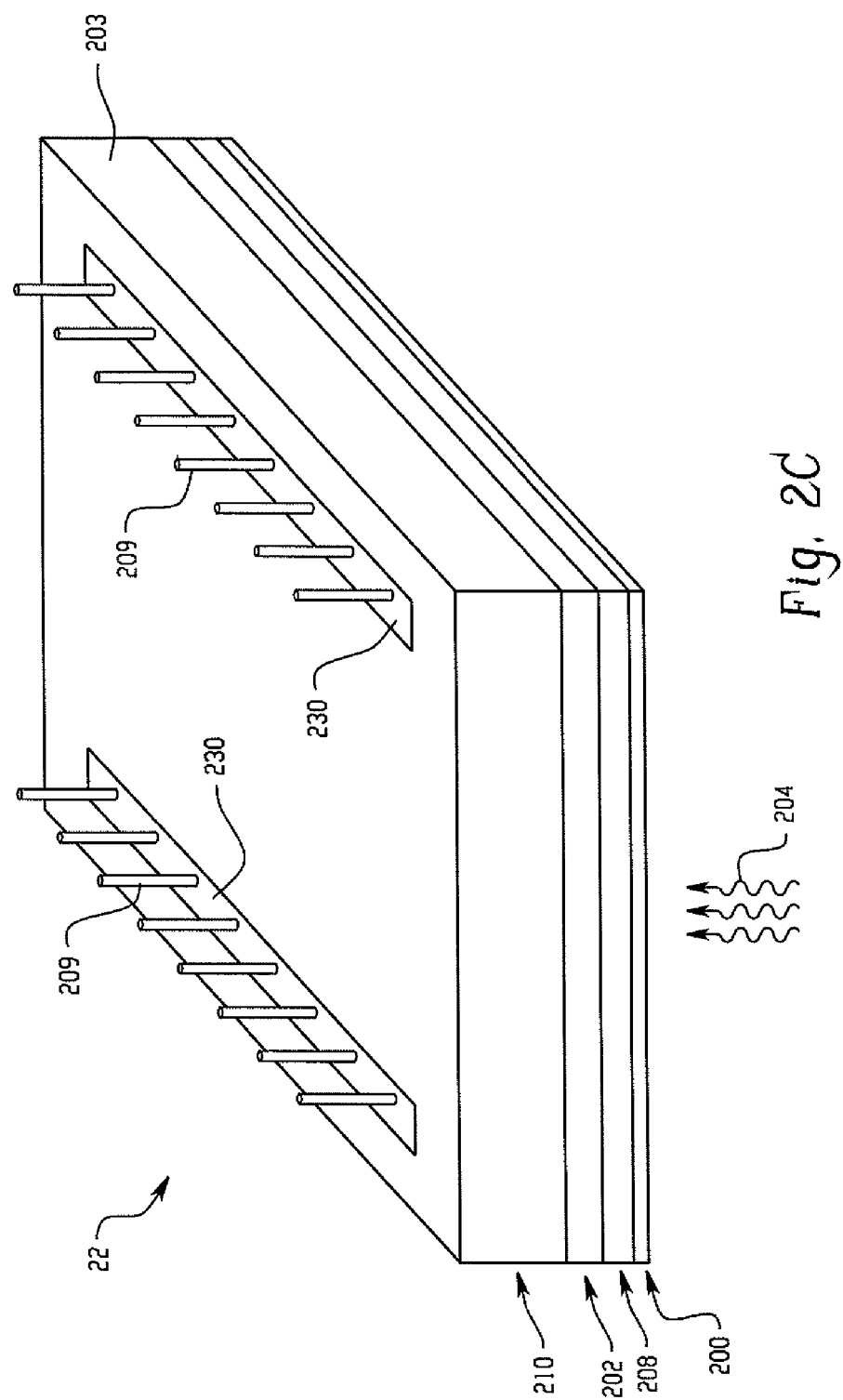

An exemplary detector module 22 is shown in FIGS. 2A, 2B, and 2C. The module 22 includes a scintillator 200, a photodetector array 202, a cover 203, readout or signal processing electronics 205, and one or more connectors 209.

The scintillator 200 is in optical communication with the photodetector array 202 so that light generated by the scintillator 200 in response to incident radiation 204 is received by a light receiving face 207 of the photodetector array 202.

The photodetector array 202 includes a semiconductor substrate 208 and metalization 210. As illustrated in FIG. 2, the substrate 208 forms a conventional BIP array in which the semiconductor 208 is doped to provide the anodes 212 and other components of the photodiodes in the array.

Metalization 210 formed on the non-illuminated side of the substrate 208 provides desired electrical interconnections and signal routing among the photodiodes and the readout electronics 205, as well as between the readout electronics 205 and the connector(s) 209. The metalization 210 is preferably formed using known CMOS or other semiconductor processing techniques as part of the fabrication of the photodetector array 202. More particularly, the metalization 210 includes alternating insulating and metal layers which are applied in the same clean room environment as the fabrication of the BIP array 208. The metal layers are typically fabricated from a conductor such as aluminum or copper, while the insulator is typically fabricated from silicon oxide (SiO), silicon dioxide ($SiO_2$), polyimide, or other suitable insulator. In any case, a uniform coating of desired metal or insulator is applied, and the layer is patterned using lithography methods to form a desired circuit pattern. The process is repeated until the desired number of metalization layers are provided. Vias provide electrical connections between the various metal layers.

As illustrated, the metalization 210 includes first $210_1$, second $210_2$, and third $210_3$ metal layers. The insulating layers are not shown for the sake of clarity. The first metalization layer $210_1$ includes connection pads 214 electrically connected to the photodiodes in the array and conductive circuit traces 221 which route the photodiode output signals as desired. The second metalization layer $210_2$ also includes connection pads 216, 219, which are accessible from the rear 228 of the photodetector array 202, and circuit traces. The third metalization layer $210_3$ serves as a ground plane. Vias 299 route the signals between the layers as needed. As illustrated, for example, the vias route signals from the first layer $210_1$ to traces and/or pads in second layer $210_2$ for connection to the input of the readout electronics 205. In this regard, it should be noted that the pads 214 and traces 221 of the first layer $210_1$ are shown as being on different planes or levels to facilitate illustration of the connections therebetween. The second layer, $210_2$ is depicted similarly. In practice, each layer is ordinarily substantially planar.

The readout electronics 205, which typically include components such as an application specific integrated circuit (ASIC) 206 and discrete components 209 such as resistors, capacitors, or other passive or active circuitry, is mounted to connecting pads. As illustrated in FIGS. 2A and 2B, the ASIC 206 is electrically connected via wire bonds 218 to pads 216, which conform to the geometry and pinout of the ASIC 206. Still other pads 217 conform to the geometry and pinout of the components 209, which are in turn soldered or otherwise connected to their respective pads 217 Also as illustrated, the connector(s) 209 are connected via solder joints 220 or otherwise connected to pads 219 which conform to the geometry and pinout of the connector(s) 209.

A particular advantage of such an arrangement is that electrical interconnections which conform to the layout and other requirements of the readout electronics 205 can be applied relatively inexpensively. Moreover, the metalization 210 can reduce the complexity of the carrier substrate which has been used to provide the various interconnections or, as shown in FIG. 2, supplant it entirely.

A radiation shield layer 222 fabricated from a radiation attenuative material such as tungsten, molybdenum or lead and located between the photodetector array 202 and the ASIC 206 may be provided to protect the ASIC 206 from the deleterious effects of ionizing radiation which is not otherwise absorbed by the scintillator 200 or the photodetector array 202. An electrostatic shield 224 (omitted from FIG. 2A for ease of illustration) may also be provided to shield some or all of the readout electronics 205 from the deleterious effects of electric fields incident from the rear of the detector module 22. A layer of thermally conductive epoxy 226 disposed between the shield 224 and the ASIC 206, and/or between the shield 224 and the cover 203, facilitates the dissipation of heat generated by the ASIC 206.

The cover 203 serves to protect the electrical circuitry 205 and the non-illuminated side 228 of the photodetector array 202. To further aid in the dissipation of heat generated by the ASIC 206, the cover 203 may be fabricated from aluminum, a thermally conductive ceramic, or other thermally conductive material. An encapsulant 230 (not shown in FIG. 2A for ease of illustration) such as an epoxy or similar compound disposed in the space between the cover 203 and the non-illuminated side 228 of the photodetector array 202 provides structural robustness and otherwise protects the readout electronics 205 from contaminants.

As illustrated, the readout electronics 205 and connectors 209 are located in a bounded plane defined by the radiation receiving face 207 of the photodetector array. As will be appreciated, such a configuration facilitates construction of tiled detector arrays.

Figure 3A:
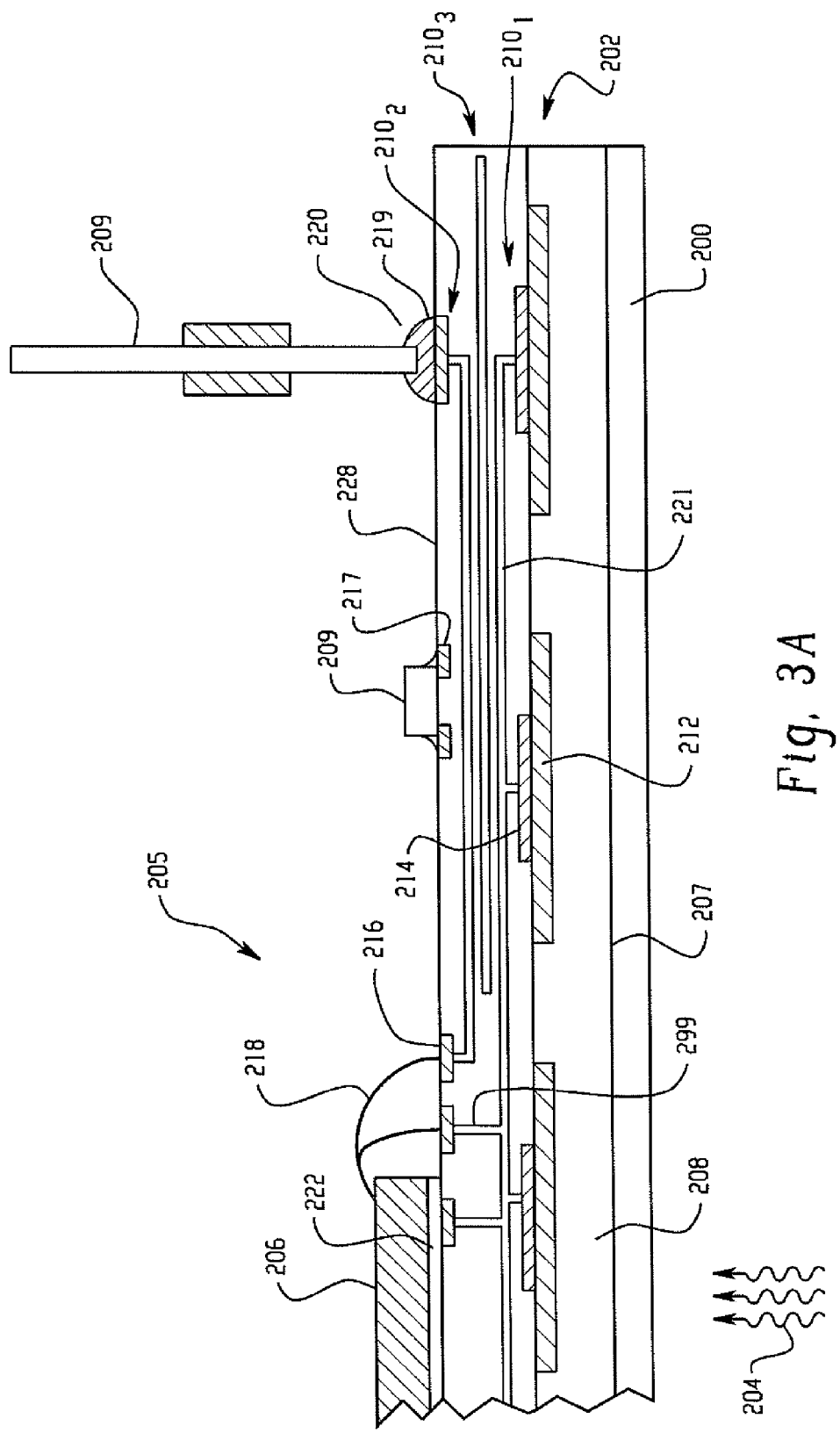
Figure 3B:
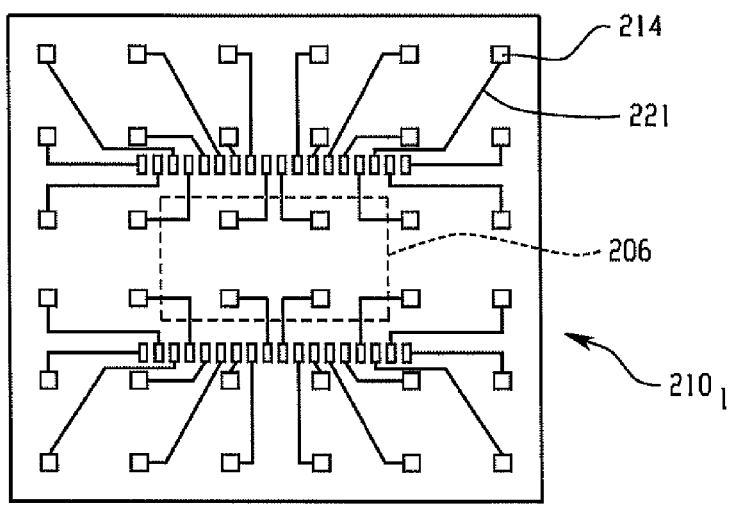
Figure 3C:
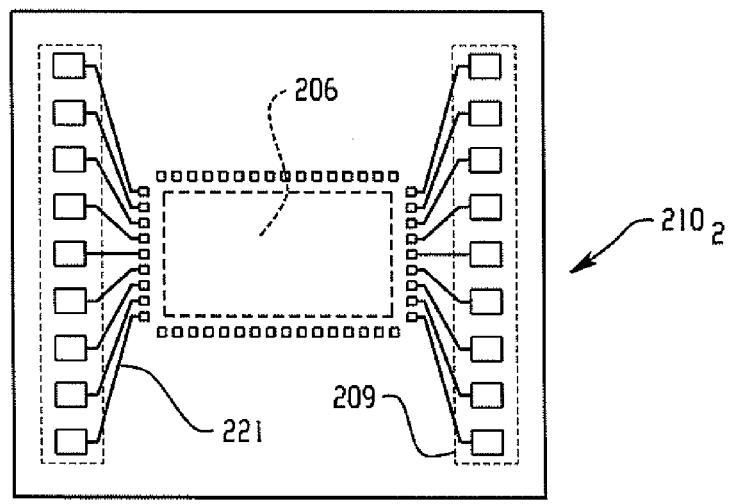
Figure 3D:
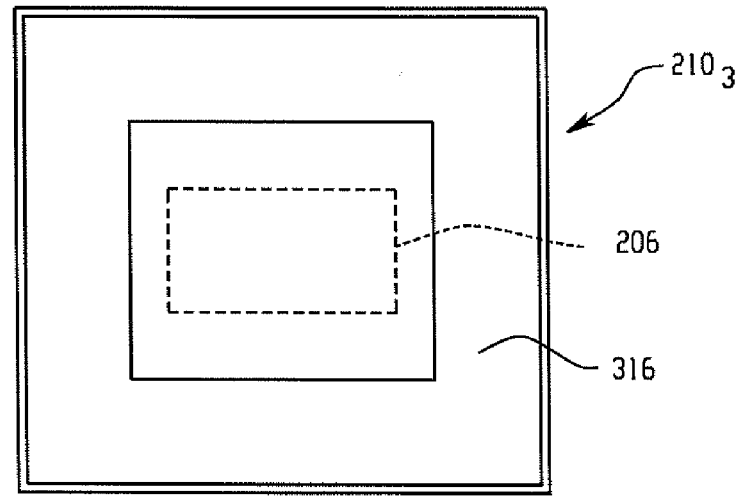

FIGS. 3A, 3B, 3C and 3D depict the photodetector array 202 and an exemplary routing of the first $210_1$, second $210_2$, and third $210_3$ metalization layers in greater detail. With reference to FIG. 3B, traces in the first metalization layer $210_1$ route the relatively low level analog signals from the various photodiode contacts 214 to the vicinity of desired connection pads 216 in the second metalization layer $210_2$. Vias connect the traces in the first layer to corresponding traces in the second metalization layer $210_2$, which traces are in turn in turn connect to the pads 216. With reference to FIG. 3C, traces in the second metalization layer $210_2$ route the generally higher level power and digital readout signals between the pads 216 and connection pads 219 which conform to the geometry and pinout of the connector(s) 209. Signals to and from other circuit elements or components may be similarly routed. Moreover, signals may also be routed directly between the photodiode pads 214 and the connector 219. With reference to FIG. 3D, the third metalization layer $210_3$ is preferably located between the first $210_1$ and second $210_2$ metalization layers and includes a ground plane or shield 316 which is electrically connected to ground.

As will be appreciated, separating the relatively low level detector signals from the power and digital signals tends to reduce undesirable coupling therebetween. Greater or lesser numbers of metalization layers 210 (e.g., one (1), two (2), or four (4) more layers) may be implemented, as the number and configuration of such layers 210 and the connections therebetween is generally a function of the density and complexity of the desired interconnections, the characteristics of the various electrical signals, as well as the desired shielding therebetween.

Figure 4:
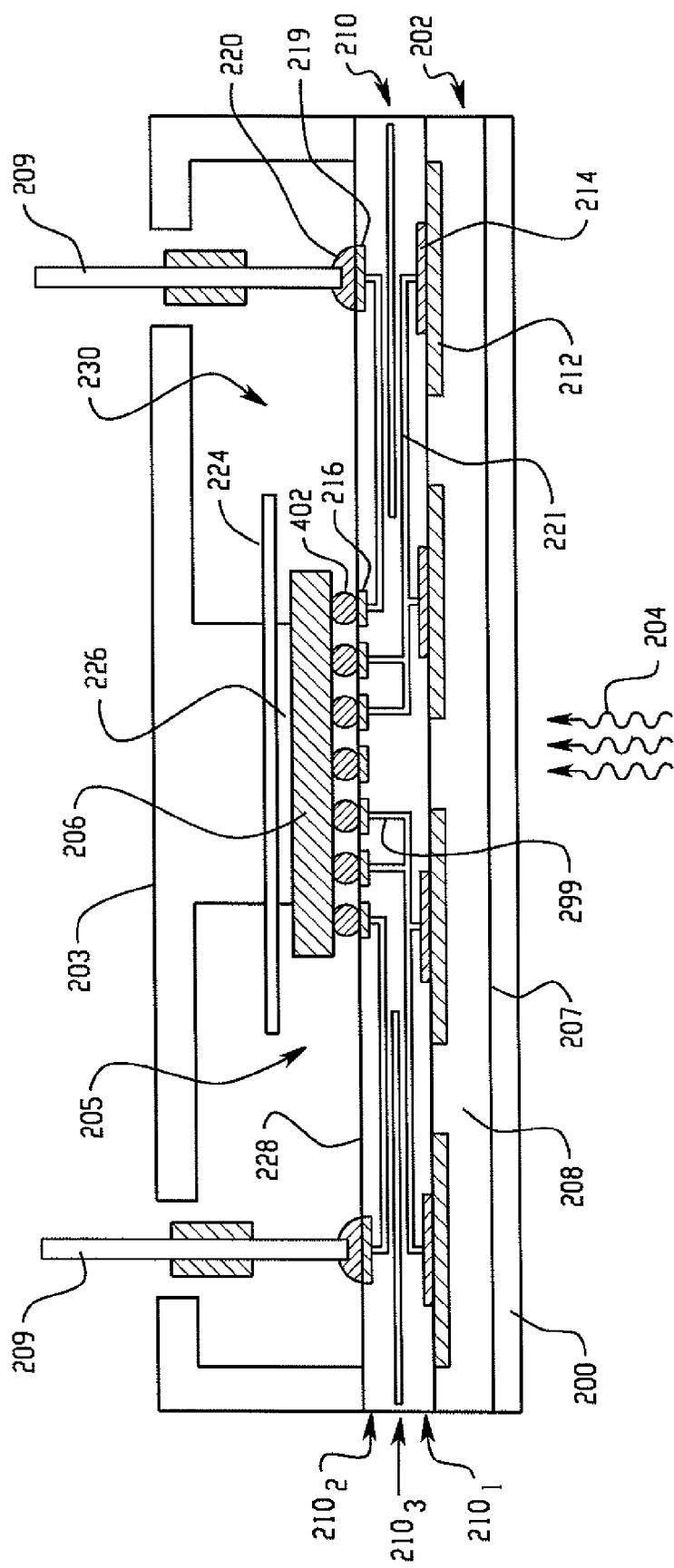
FIG. 4 depicts a detector module.

While the ASIC 206 has been described as being wire-bonded to its corresponding pads 216, it may also be flip chip or bump bonded to suitably configured connecting pads 216 using solder bumps 402 as shown in FIG. 4.

Figure 5:
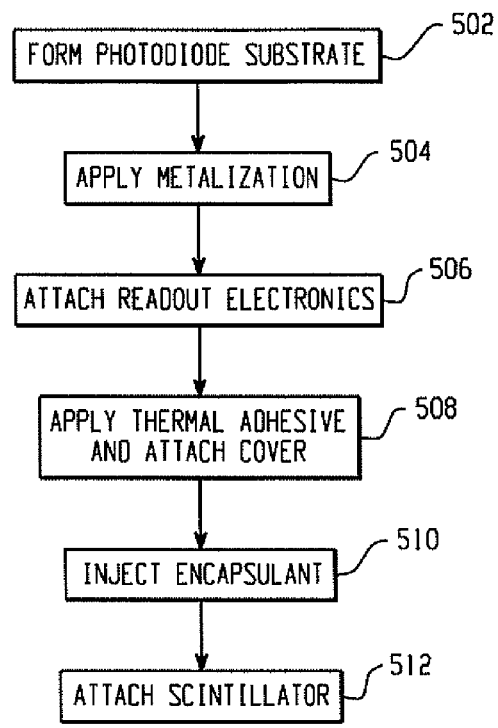
FIG. 5 depicts steps in manufacturing a detector module.

Fabrication of the detector module 22 will now be described with reference to FIGS. 5 and 6.

Figure 6A:
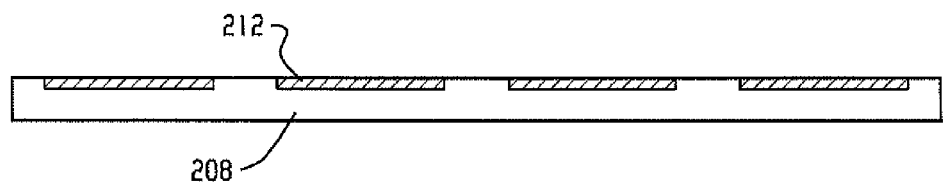

At step 502, and with reference to FIG. 6A, the substrate 208 is processed, for example to produce a conventional BIP array.

Figure 6B:
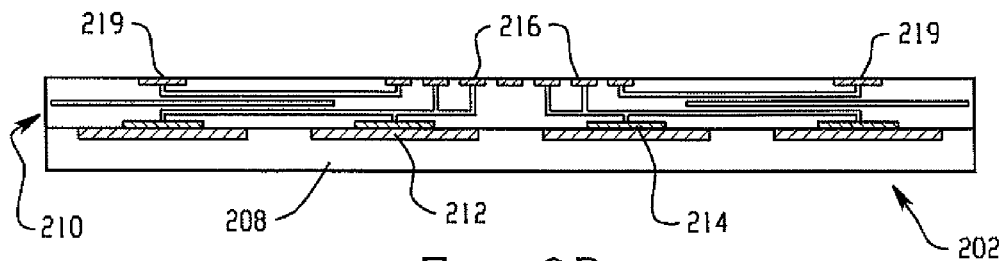

At step 504, and with reference to FIG. 6B, the desired metalization 210 is applied to the non-illuminated side of the substrate 208 to form the photodetector array 202.

Figure 6C:
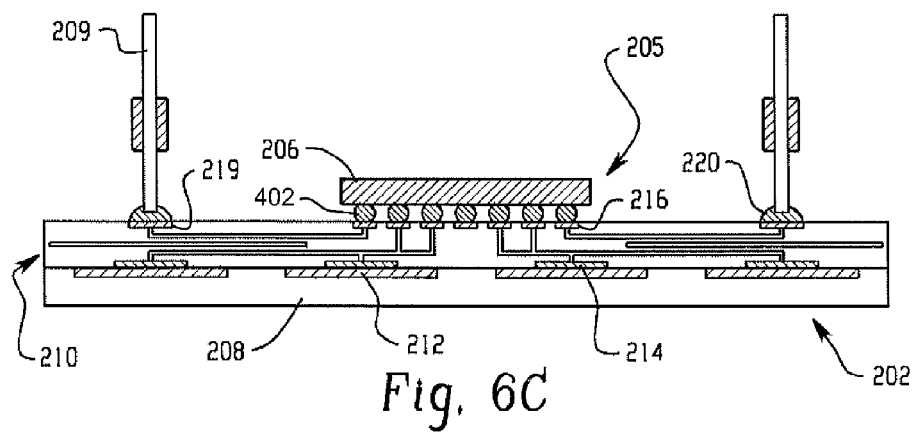

At step 506, and with reference to FIG. 6C, the various components of the readout electronics 208 are attached to the backside of the photodetector array 202, for example by way of a reflow soldering operation in which the readout electronics 205 and connectors 209 are soldered to the corresponding pads 216, 217, 219 formed on the rear surface 228 of the metalization 210. Where the ASIC 206 or other components are connected via wire bonds 218, the desired wire-bonds are also applied. Where utilized, the radiation shield 222 would typically be installed prior to the soldering or wire-bonding operation, as applicable. Note that conductive epoxy or other suitable materials may also be used in place of solder where desired.

Figure 6D:
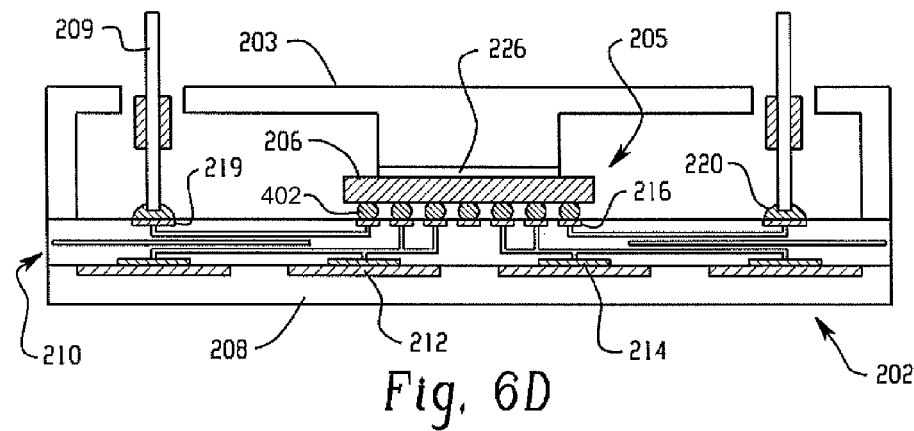

At step 508, and with reference to FIG. 6D, the thermally conductive adhesive 226 and electrostatic shield 224 (if any) are applied, and the cover 203 is installed.

Figure 6E:
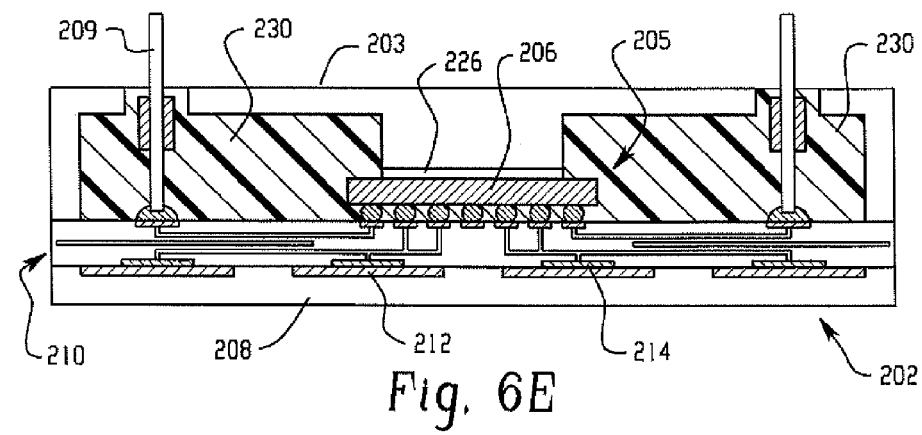

At step 510, and with reference to FIG. 6E, the encapsulant 230 is injected in the space or spaces between the cover 203 and the back side of the array 202.

At step 512, the scintillator 200, if any, is attached to the light receiving face 207 of the array 202.

FIGS. 7A and 7B depict alternative cover arrangements. As illustrated in FIG. 7A, the cover 203 is formed from a first cover portion 203a and a thermally conductive cover portion 203b. The first cover portion 203a is injection molded or otherwise fabricated from a relatively inexpensive material such as a plastic or other polymer. The thermally conductive portion 203b is fabricated from a relatively more thermally conductive material such as aluminum or a thermally conductive ceramic. The first 203a and second 204b portions are joined following fabrication of the first portion 203a. Alternately, the first cover portion 203a may be molded or otherwise formed around the thermally conductive cover portion 203b. In any case, the thermally conductive portion 203b is preferably configured to provide relatively efficient thermal conduction path which aids in the dissipation of heat generated by the ASIC 206 or other desired portions of the readout electronics 205.

With reference to FIG. 7B, the detector module 22 is provided with a thermally conductive member 702 which is analogous the thermally conductive cover portion 203b described above in relation to FIG. 7A. Following installation of the conductive member 703a, a protective covering 704 such as a polymer or encapsulant is then molded or otherwise applied to the rear of the detector module 22.

Still other variations are possible. For example, the photodetector array 202 may be implemented using front illuminated photodiodes in which the photodiode electrical connections are formed on the illuminated side of the array. In such a case, the photodetector array 202 is advantageously provided with through holes or vias which route the photodiode signals to the non-illuminated side of the photodetector array 202. The photodetector array 202 may also be produced using suitable photodetector or photodiode technologies such as positive intrinsic negative (PIN) photodiodes, complementary metal oxide semiconductor (CMOS) photodetectors, or avalanche photodiodes operating in the linear or single photon modes.

As will also be appreciated, the scintillator 200 may be fabricated from a conventional scintillator material such as gadolinium oxysulfide (GOS) or cadmium tungstate ($CdWO_4$) which is ordinarily selected based on the spectral, response time, and other requirements of a particular application, The scintillator 200 may also be omitted, particularly in applications in which the detector module 22 is used to detect light radiation or radiation of a wavelength which corresponds to the spectral response of the photodetector array 202. Spectral radiation detectors which produce outputs indicative of more than one energy spectra are also contemplated.

The detector modules 22 may also be assembled to form one or more detector subassemblies which are in turn assembled to form a generally arcuate detector array. Turning now to FIGS. 8A and 8B, a detector subassembly 800 includes a plurality of detector modules $22_1, 22_2 \ldots 22_n$, a circuit board 802, and a support 804. The circuit board 802 includes material free regions $806_1, 806_2 \ldots 806_n$ and a connector 808. The connectors 209 of the detector modules 22 are soldered or otherwise connected to a first side of the circuit board 802. The circuit board 802 carries conductive traces 812 which connect the detector modules 22 to the connector 808. The illustrated trace 812 configuration is particularly advantageous where the detector modules 22 produce digital outputs which can be daisy chained.

The support 804, which is advantageously fabricated from metal or other thermally conductive material, attaches from the second side of the circuit board 802. The support 804 includes protrusions 810 which pass through the material free regions to make thermal contact with the covers 203, and more particularly the thermally more conductive cover portions, of the various detector modules 22. The support 804 is in turn used mount the subassembly 800 as part of a larger, generally arcuate detector array for use in a CT scanner or other desired application.

A particular advantage of the foregoing arrangement is that the various detector modules 22 may be aligned relative to each other and to the circuit board 802 prior to the soldering operation. According to such an arrangement, the tolerances of the individual detectors 22 are less critical, and the circuit board 802 serves as a reference for the registration of multiple sub-assemblies 800.

Alternate configurations of a detector subassembly 900 are shown in FIGS. 9A, 9B, and 9C. The detector modules 22 are fastened to a support 902 using screws 904 or other suitable fasteners. The connectors 209 of the various detector modules 22 are in turn soldered to circuit boards 904a, 904b.

Another detector subassembly configuration is shown in FIGS. 10A and 10B. As illustrated, a detector subassembly 1000 includes a plurality of detector modules $22_1, 22_2 \ldots 22_n$ and first 1002 and second 1004 circuit boards. The connectors 209 of the detector modules 22 are soldered or otherwise connected to the first circuit board 1002. One more heat sinks may be placed between the detector modules 22 and the first circuit board 1002 and in thermal communication with the covers 203. Electrical connections 1006 between the circuit boards 1002, 1004 are provided through flexible circuits or other suitable connections. Mechanical connections between the circuit boards 1002, 1004 are provided by way of suitable arrangements such as brackets 808, adhesive connections, or the like. The second circuit board 1004 may also be implemented as a flexible circuit, thus obviating the need for the connections 1006.

With reference to FIG. 11, a desired plurality of detector sub-assemblies such as subassemblies $900_1, 900_2, 900_3, 900_4, 900_5$ are in turn assembled so as to form a generally arcuate detector array of the desired angular extent.

Of course, modifications and alterations will occur to others upon reading and understanding the preceding description. It is intended that the invention be construed as including all such modifications and alterations insofar as they come within the scope of the appended claims or the equivalents thereof.

What is claimed is:

1. A radiation detector comprising:
   a scintillator;
   a photodetector array comprising:
      a semiconductor substrate, including: a plurality of photodetector elements in optical communication with the scintillator; and
      a CMOS metalization side, opposite the scintillator, wherein the metallization side includes alternating insulating and metal layers and is a part of the semiconductor substrate; and
      signal processing electronics carried on a side of the photodetector array opposite the scintillator;
   wherein the metalization side includes a first plurality of contacts electrically connected to the photodetector elements, a second plurality of contacts in electrical communication with the first plurality of contacts and the signal processing electronics, wherein the metalization side includes a first metalization layer that connects at least one discrete component and the second plurality of contacts, a second metalization layer that connects the first plurality of contacts to the second plurality of contacts, and a third metalization layer located between at least a portion of the first metalization layer and at least a portion of the second metalization layer.

2. The radiation detector of claim 1 wherein the first plurality of contacts is disposed in the first layer, the second plurality of contacts is disposed in the second layer, and a ground plane is disposed in the third layer.

3. The radiation detector of claim 2 wherein the first plurality of contacts routes analog signals from the photodetector elements to the signal processing electronics, the second plurality of contacts routes digital signals from the signal processing electronics to readout electronics, and the ground plane electrically decouples the analog and digital signals.

4. The radiation detector of claim 1 wherein the signal processing electronics includes an integrated circuit.

5. The radiation detector of claim 4 wherein the integrated circuit is bump bonded to the second plurality of contacts.

6. The radiation detector of claim 1 wherein the metalization includes electrically conductive circuit traces which form at least a portion of an electrically conductive path between the first plurality of contacts and the second plurality of contacts.

7. The radiation detector of claim 1 including a cover which includes a first portion fabricated from a relatively thermally insulative material and second portion fabricated from a relatively thermally conductive material, wherein the signal processing electronics includes an integrated circuit, and wherein the second portion provides a thermally conductive path between the integrated circuit and an exterior of the radiation detector.

8. The radiation detector of claim 1 wherein the plurality of photodetector elements are arranged in an array which defines a bounded plane, and wherein the signal processing electronics are disposed within the bounded plane.

9. The radiation detector of claim 1, wherein the CMOS metallization side of the semiconductor substrate with the photodetector is an applied CMOS layer of the semiconductor substrate with the photodetector.

10. The radiation detector of claim 1, wherein the CMOS metallization side of the semiconductor substrate with the photodetector is not part of a donor wafer with electronics that is bonded to the semiconductor substrate with the photodetector through wafer-to-wafer bonding or die-to-wafer bonding.

11. The radiation detector of claim 1, wherein the CMOS metallization side of the semiconductor substrate with the photodetector includes a plurality of sequentially applied CMOS layers.

12. The radiation detector of claim 1, further comprising: at least one of a solder or a wire bond between the CMOS metallization side of the semiconductor substrate with the photodetector and the signal processing electronics.

13. A semiconductor substrate of a radiation detector comprising:
 a two dimensional array of photodetector elements which detect radiation; and
 a CMOS metalization side of the semiconductor substrate which is opposite the array of photodetector elements, wherein the metalization includes first contacts and second contacts, the metalization side, comprising:
  a first metal layer configured to connect the first contacts, which are electrically connected to the array of photodetector elements, and the second contacts;
  a second metal layer configured to connect the second contacts and at least one discrete component of readout electronics; and
  a third metal layer located between at least a portion of the first metal layer and at least a portion of the second metal layer.

14. The semiconductor substrate of claim 13, wherein the array of photodetector elements has a first physical layout, wherein the semiconductor substrate is adapted for use with signal processing electronics having a second physical layout which is different from the first physical layout, and wherein the second contacts conform to the second physical layout.

15. The semiconductor substrate of claim 14 wherein semiconductor substrate is adapted for use with signal processing electronics which are wire bonded to the second contacts.

16. The semiconductor substrate of claim 13 wherein the metalization includes electrical conductors which provide at least a portion of electrically conductive paths between the first and second contacts.

17. The semiconductor substrate of claim 16 wherein the third metal layer is a shield, electrically connected to ground, that electrically decouples analog signals routed from the array of photodetector elements by the first contacts to the second contacts and digital signals routed from the second contacts to the readout electronics.

18. The semiconductor substrate of claim 13 wherein the metalization includes contacts adapted to connect to an electrical connector.

19. The semiconductor substrate of claim 18 further including an electrical connector and a circuit board, wherein the electrical connector is connected to the contacts adapted to connect to the electrical connector and to the circuit board so as provide an electrical connection therebetween.

* * * * *